United States Patent [19]

Szmuszkovicz

[11] 3,933,816

[45] *Jan. 20, 1976

[54] 3-(SUBSTITUTED AMINOMETHYL)-7-SUBSTITUTED-3,5-DIHYDRO-AS-TRIAZINO[4,3-A][1,5]BENZODIAZEPINES

[75] Inventor: Jacob Szmuszkovicz, Kalamazoo, Mich.

[73] Assignee: The Upjohn Company, Kalamazoo, Mich.

[ * ] Notice: The portion of the term of this patent subsequent to May 6, 1992, has been disclaimed.

[22] Filed: Sept. 12, 1974

[21] Appl. No.: 505,507

[52] U.S. Cl. ..... 260/248 AS; 260/247.5 C; 424/249; 260/239 BD; 260/294.8 C
[51] Int. Cl.² ..................................... C07D 251/72
[58] Field of Search ................ 260/248 AS, 247.5 C

[56] References Cited
UNITED STATES PATENTS 3,818,003  6/1974  Szmuszkovicz .................... 260/248

*Primary Examiner*—John M. Ford
*Attorney, Agent, or Firm*—Hans L. Berneis

[57] ABSTRACT

A compound of the formula:

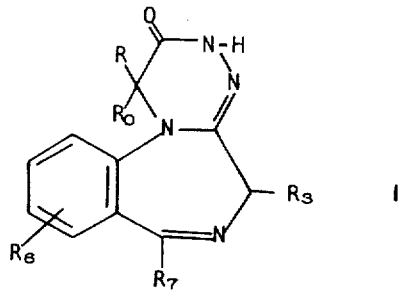

wherein R, $R_0$, and $R_3$ are hydrogen or alkyl of 1 to 3 carbon atoms, inclusive; wherein $R_1$ and $R_2$ are alkyl of 1 to 3 carbon atoms, or the group

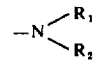

together is pyrrolidino, piperidino, morpholino and N-methylpiperazino; wherein $R_7$ is 2-pyridyl or a phenyl radical of the formula

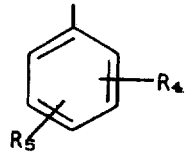

wherein $R_4$ is hydrogen, fluoro, or chloro; wherein $R_5$ is hydrogen or fluoro, with the proviso that $R_5$ is not fluoro, when $R_4$ is chloro; and wherein $R_6$ is hydrogen, chloro, fluoro, bromo, trifluoromethyl, or nitro.

The new compounds of formula II have tranquilizing and antianxiety activity and are thus useful to treat mammals and birds.

15 Claims, No Drawings

3,933,816

3-(SUBSTITUTED AMINOMETHYL)-7-SUBSTITUTED-3,5-DIHYDRO-AS-TRIAZINO[4,3-A][1,5]BENZODIAZEPINES

BACKGROUND OF THE INVENTION

FIELD OF THE INVENTION

This invention is directed to new organic compounds and is more particularly concerned with novel 7-substituted-3-(aminomethyl)-3,5-dihydro-as-triazino[4,3-a][1,4]benzodiazepin-2-(1H)-ones and a process of production therefor.

The novel compounds II and the process of production therefor can be illustratively represented as follows:

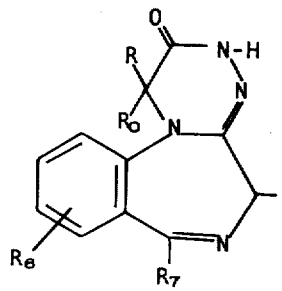

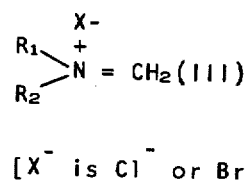

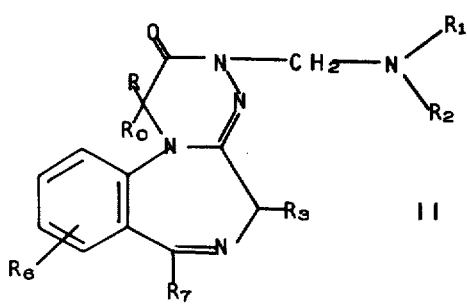

wherein R, $R_o$, and $R_3$ are hydrogen or alkyl of 1 to 3 carbon atoms, inclusive; wherein $R_1$ and $R_2$ are alkyl of 1 to 3 carbon atoms, or the group

together is pyrrolidino, piperidino, morpholino and N-methylpiperazino; wherein $R_7$ is 2-pyridyl or a phenyl radical of the formula

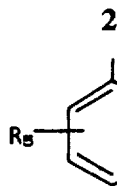

in which $R_4$ is hydrogen, fluoro, or chloro; wherein $R_5$ is hydrogen or fluoro, with the proviso that $R_5$ is not fluoro, when $R_4$ is chloro; and wherein $R_6$ is hydrogen, chloro, fluoro, bromo, trifluoromethyl, or nitro.

The more desirable products of this invention are of the formula:

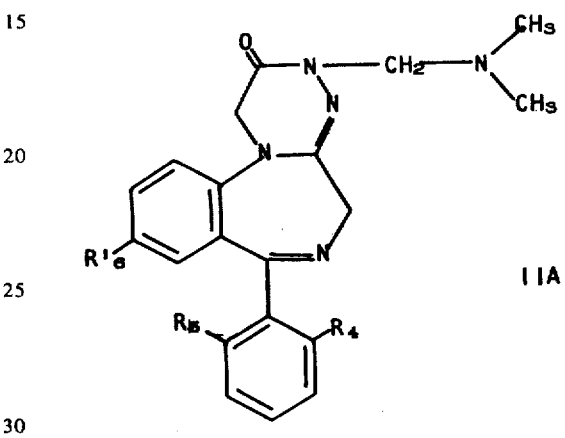

wherein $R_4$ is hydrogen, chloro, or fluoro; wherein $R_5$ is not fluoro, when $R_4$ is chloro; and wherein $R'_6$ is chloro, fluoro, trifluoromethyl, or nitro.

The most preferred compounds are of the formula

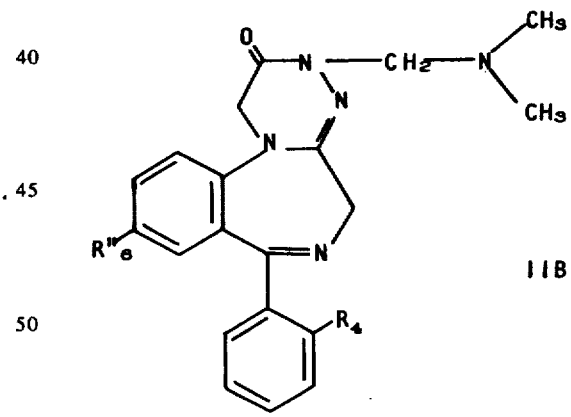

$R''_6$ is chloro, trifluoromethyl or fluoro; and $R_4$ is hydrogen, chloro or fluoro.

The process of this invention comprises: heating a compound of formula I with a strong base in an inert organic solvent, and then treating the resulting solution with a selected methylene ammonium chloride or bromide of formula III.

DESCRIPTION OF THE PREFERRED EMBODIMENT

Alkyl groups of 1 to 3 carbon atoms, inclusive, are exemplified by methyl, ethyl, propyl, and isopropyl.

The novel compounds of the formula II (and also IIA and IIB), have sedative, tranquilizing and muscle-relaxant effects in mammals and birds.

Sedative effects of these compounds of formula II (IIA and IIB included), were measured by standard procedures used in the art, and as shown below:

Chimney test: [Med. Exp. 4, 145 (1961)]: The test determines the ability of mice to back up and out of a vertical glass cylinder within 30 seconds. At the effective dosage ($ED_{50}$), 50% of the mice are unable to pass this test.

Dish test: Mice in Petri dishes (10 cm. diameter, 5 cm. high, partially embedded in wood shavings), climb out in a very short time, when not treated. Mice remaining in the dish for more than 3 minutes indicates tranquilization. $ED_{50}$ equals the dose of test compound at which 50% of the mice remain in the dish.

Pedestal test: The untreated mouse leaves the pedestal in less than a minute to climb back to the floor of the standard mouse box. Tranquilized mice will stay on the pedestal for more than 1 minute.

Nicotine antagonism test: Mice in a group of 6 are injected with the test compound. Thirty minutes later the mice, including control (untreated) mice, are injected with nicotine salicylate (2 mg./kg.). The control mice show overstimulation, i.e., (1) running convulsions followed by (2) tonic extensor fits; followed by (3) death.

These compounds also had minor anti-depressant activity as shown by standard tests.

The pharmaceutical forms contemplated by this invention include pharmaceutical compositions suited for oral, parenteral and rectal use, e.g., tablets, powder packets, cachets, dragees, capsules, solutions, suspensions, sterile injectable forms, suppositories, bougies, and the like. Suitable diluents or carriers such as carbohydrates (lactose), proteins, lipids, calcium phosphate, cornstarch, stearic acid, methylcellulose and the like may be used as carriers or for coating purposes. Water and oils, e.g., coconut oil, sesame oil, safflower oil, cottonseed oil, and peanut oil may be used for preparing solutions or suspensions of the active drug. Sweetening, coloring, and flavoring agents may be added.

For mammals and birds food premixes, with starch, oatmeal, dried fishmeat, fishmeal, flour, and the like can be prepared.

As tranquilizer and anti-anxiety agents, the compounds of formulae II (including IIA and IIB) can be used in dosages of 0.01 mg. to 0.3 mg./kg., preferably 0.01 to 0.15 mg./kg. in oral or injectable preparations as described above, to alleviate tension and anxiety in mammals, or birds, such as, e.g., occurs when animals are in travel. For larger animals, in excess of 5 kg. the lower-dosage ranges are indicated.

The starting compounds of formula I can be prepared as shown in U.S. Pat. No. 3,236,838, and in the preparations.

The reagent of formula III can be prepared as described by Böhme et al., Ber. 93, 1305 (1960) e.g. by reacting for example N,N,N',N'-tetramethyldiaminomethane with acetyl chloride, thus:

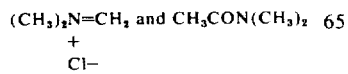

or bis(piperidino)methane with acetyl chloride, thus:

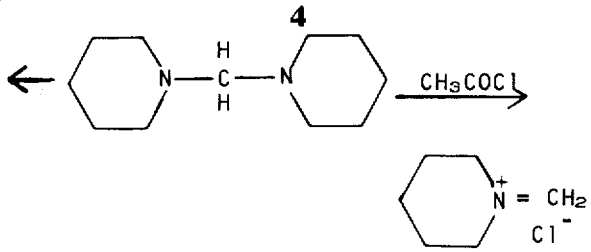

In carrying out the process of this invention the selected starting compound I is added to a suspension of a base in an inert organic solvent. As base sodium hydride, lithium hydride, sodium or potassium ethoxide and the like may be used. As suspending agent dimethylformamide, diethylformamide, dimethylacetamide, xylenes or the like may be used. In the preferred embodiment of this invention equimolecular quantities of compound I and the base are heated between 75° and 120° C. To the resulting solution after cooling is added the selected methylene ammonium chloride III and the mixture is heated for 6 to 24 hours between 75° to 120° C. The resulting product of formula II, a 7-substituted-3-(aminomethyl)-3,5-dihydro-as-triazino[4,3-a][1,4]benzodiazepine-2H-(1)-one, is recovered by conventional methods known in the art, e.g., evaporation of the reaction mixture, extraction, crystallization, chromatography or the like.

The following preparations and examples are illustrative of the products and processes of the present invention, but are not to be construed as limiting.

The preparation of starting compounds of formula I is carried out according to the scheme below:

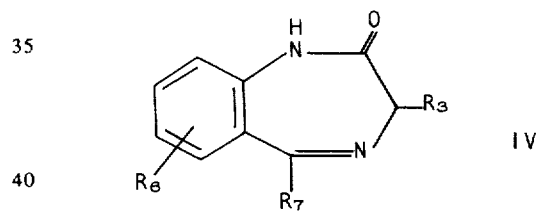

IV

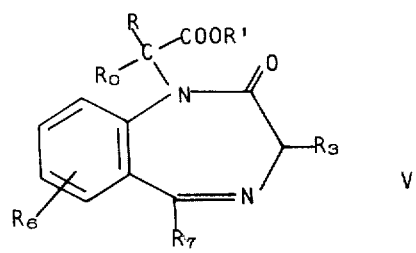

V

↓ from V

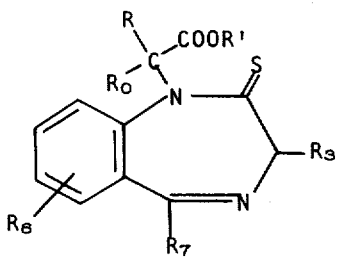

↓ NH₂-NH₂

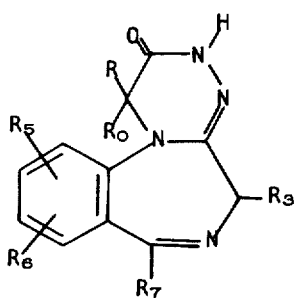

Preparation 1

7-Chloro-2,3-dihydro-2-oxo-5-phenyl-1H-1,4-benzodiazepine-1-acetic acid methyl ester Sodium methoxide (5.95 g., 0.11 mole) is added to a solution of 7-chloro-1,3-dihydro-5-phenyl-2H-1,4-benzodiazepin-2-one (27 g., 0.1 mole) in 200 ml. of dimethylformamide and the mixture is stirred and heated on a steambath for about 20 minutes. To this mixture is added a solution of methyl bromoacetate (16.7 g., 0.11 mole) in 165 ml. of toluene during 1 hour while stirring and heating are continued. The mixture is heated for an additional 2 hours, allowed to stand overnight at room temperature (about 25° C.) and evaporated to dryness in vacuo. The residue is stirred with 500 ml. of water until a suspension results. The suspension is filtered and the solid thus obtained is crystallized first from ether and then from ethanol to give 14.5 g. (42% yield) of 7-chloro-2,3-dihydro-2-oxo-5-phenyl-1H-1,4-benzodiazepine-1-acetic acid methyl ester of melting point 137°–138° C.

Preparation 2

7-Chloro-5-(o-chlorophenyl)-2,3-dihydro-2-oxo-1H-1,4-benzodiazepine-1-acetic acid methyl ester Sodium methoxide (5.95 g., 0.11 mole) is added to a solution of 7-chloro-1,3-dihydro-5-(o-chlorophenyl)-2H-1,4-benzodiazepin-2-one (30.5 g., 0.1 mole) in 200 ml. of dimethylformamide and the mixture is heated at 95° for about 15 minutes. To the mixture is added a solution of methyl bromoacetate (16.7 g., 0.11 mole) in 165 ml. of toluene during 55 minutes while heating is continued. After heating the mixture for an additional 6.25 hours, it is evaporated to dryness, and the residue is stirred with 400 ml. of water and 200 ml. of ether. The resulting suspension is filtered and the solid thus obtained is crystallized from methylene chloride-methanol to give 24.9 g. of 7-chloro-5-(o-chlorophenyl)-2,3-dihydro-2-oxo-1H-1,4-benzodiazepine-1-acetic acid methyl ester of melting point 193°–194° C.

Anal. Calcd. for $C_{18}H_{14}Cl_2N_2O_3$: C, 57.31; H, 3.74; Cl, 18.80; N, 7.43. Found: C, 57.38; H, 4.03; Cl, 18.92; N, 7.55.

Preparation 3

5-(o-chlorophenyl)-2,3-dihydro-2-oxo-1H-1,4-benzodiazepin-1-acetic acid methyl ester Sodium methoxide (2.26 g., 0.042 mole) is added to a solution of 5-(o-chlorophenyl)-1,3-dihydro-2H-1,4-benzodiazepin-2-one (10.3 g., 0.038 mole) in 100 ml. of dimethylformamide and the mixture is heated at 95° for about 25 minutes. To the mixture is added a solution of methyl bromoacetate (6.4 g., 0.042 mole) in 65 ml. of toluene during 45 minutes while heating is continued. The mixture is heated for an addiitional 5.5 hours and allowed to stand overnight. It is evaporated to dryness and the residue is stirred with a mixture of 150 ml. of water and 150 ml. of ether. The resulting suspension is filtered, and the solid thus obtained is crystallized from methanol to give 7.9 g. of 5-(o-chlorophenyl)-2,3-dihydro-2-oxo-1H-1,4-benzodiazepin-1-acetic acid methyl ester of melting point 166°–167.5° C.

Anal. Calcd. for $C_{18}H_{15}ClN_2O_3$: C, 63.07; H, 4.41; Cl, 10.34; N, 8.17. Found: C, 62.87; H, 4.44; Cl, 10.38; N, 8.17.

PREPARATION 4

7-Chloro-2,3-dihydro-2-oxo-5-(2,6-difluorophenyl)-1H-1,4-benzodiazepin-1-acetic acid methyl ester A mixture of 0.1 mole of 7-chloro-1,3-dihydro-5-(2,6-difluorophenyl)-2H-1,4-benzodiazepin-2-one and 0.11 mole of sodium methoxide in about 200 ml. of dimethylformamide is heated at about 95° C. for about 20 minutes. To the mixture is added a solution of 0.11 mole of methyl bromoacetate in about 200 ml. of toluene over a period of about 1 hour at about 95° C., and heating is continued for an additional period of about 6 hours. The reaction mixture is then evaporated in vacuo and the residue thus obtained is stirred with about 500 ml. of water. The resulting suspension is filtered and the solids thus obtained are crystallized from a suitable organic solvent such as ether, methanol, methylene chloride, methylene chloride-methanol and the like to obtain 7-chloro-2,3-dihydro-2-oxo-5-(2,6-difluorophenyl)-1H-1,4-benzodiazepin-1-acetic acid methyl ester.

PREPARATION 5

7-(Trifluoromethyl)-2,3-dihydro-2-oxo-5-phenyl-1H-1,4-benzodiazepin-1-acetic acid ethyl ester A mixture of 0.1 mole of 7-(trifluoromethyl)-1,3-dihydro-5-phenyl-2H-1,4-benzodiazepin-2-one and 0.11 mole of sodium methoxide in about 200 ml. of dimethylformamide is heated at about 95° C. for about 20 minutes. To the mixture is added a solution of 0.11 mole of ethyl bromoacetate in about 200 ml. of toluene over a period of about 1 hour at about 95° C., and heating is continued for an additional period of about 6 hours. The reaction mixture is then evaporated in vacuo and the residue thus obtained is stirred with about 500 ml. of water. The resulting suspension is filtered and the solids thus obtained are crystallized from a suitable organic solvent such as ether, methanol, methylene chloride, methylene chloride-methanol and the like to obtain 7-(trifluoromethyl)-b 2,3-dihydro-2-oxo-5-phenyl-1H-1,4-benzodiazepin-1-acetic acid ethyl ester.

PREPARATION 6

7-Chloro-2,3-dihydro-α,α-dimethyl-2-oxo-5-phenyl-1H-1,4-benzodiazepin-1-acetic acid methyl ester A mixture of 0.1 mole of 7-chloro-1,3-dihydro-5-phenyl-2H-1,4-benzodiazepin-2-one and 0.11 mole of sodium methoxide in about 200 ml. of dimethylformamide is heated at about 95° C. for about 20 minutes. To the mixture is added a solution of 0.11 mole of methyl 2-bromo-2-methylpropionate in about 200 ml. of toluene over a period of about 1 hour at about 95° C., and heating is continued for an additional period of about 6 hours. The reaction mixture is then evaporated in vacuo and the residue thus obtained is stirred with about 500 ml. of water. The resulting suspension is filtered and the solids thus obtained are crystallized from a suitable organic solvent such as ether, methanol, methylene chloride, methylene chloride-methanol and the like to obtain 7-chloro-2,3-dihydro-α,α-dimethyl-2-oxo-5-phenyl-1H-1,4-benzodiazepin-1-acetic acid methyl ester.

PREPARATION 7

7-Nitro-2,3-dihydro-2-oxo-5-(o-chlorophenyl)-1H-1,4-benzodiazepin-1-acetic acid propyl ester A mixture of 0.1 mole of 7-nitro-1,3-dihydro-5-(o-chlorophenyl)-2H-1,4-benzodiazepin-2-one and 0.11 mole of sodium methoxide in about 200 ml. of dimethylformamide is heated at about 95° C. for about 20 minutes. To the mixture is added a solution of 0.11 mole of propyl bromoacetate in about 200 ml. of toluene over a period of about 1 hour at about 95° C., and heating is continued for an additional period of about 6 hours. The reaction mixture is then evaporated in vacuo and the residue thus obtained is stirred with about 500 ml. of water. The resulting suspension is filtered and the solids thus obtained are crystallized from a suitable organic solvent such as ether, methanol, methylene chloride, methylene chloride-methanol and the like to obtain 7-nitro-2,3-dihydro-2-oxo-5-(o-chlorophenyl)-1H-1,4-benzodiazepin-1-acetic acid propyl ester.

PREPARATION 8

9-Bromo-2,3-dihydro-2-oxo-5-(m-fluorophenyl)-3,α-dimethyl-1H-1,4-benzodiazepin-1-acetic acid methyl ester.

A mixture of 0.1 mole of 9-bromo-1,3-dihydro-5-(m-fluorophenyl)-3-methyl-2H-1,4-benzodiazepin-2-one and 0.11 mole of sodium methoxide in about 200 ml. of dimethylformamide is heated at about 95° C. for about 20 minutes. To the mixture is added a solution of 0.11 mole of methyl 2-bormopropionate in about 200 ml. of toluene over a period of about 1 hour at about 95° C., and heating is continued for an additional period of about 6 hours. The reaction mixture is then evaporated in vacuo and the residue thus obtained is stirred with about 500 ml. of water. The resulting suspension is filtered and the solids thus obtained are crystallized from a suitable organic solvent such as ether, methanol, methylene chloride, methylene chloride-methanol and the like to obtain 9-bromo-2,3-dihydro-2-oxo-5-(m-fluorophenyl)-3, α-dimethyl-1H-1,4-benzodiazepin-1-acetic acid methyl ester.

PREPARATION 9

7-Fluoro-5-(o-chlorophenyl)-2,3-dihydro-3-ethyl-α,α-dimethyl-2-oxo-1H-1,4-benzodiazepin-1-acetic acid methyl ester A mixture of 0.1 mole of 7-fluoro-1,3-dihydro-5-o-chlorophenyl)-127  3-ethyl-2H-1,4-benzodiazepin-2-one and 0.11 mole of sodium methoxide in about 200 ml. of dimethylformamide is heated at about 95° C. for about 20 minutes. To the mixture is added a solution of 0.11 mole of methyl 2-bromo-2-methyl-propionate in about 200 ml. of toluene over a period of about 1 hour at about 95° C., and heating is continued for an additional period of about 6 hours. The reaction mixture is then evaporated in vacuo and the residue obtained is stirred with about 500 ml. of water. The resulting suspension is filtered and the solids thus obtained are crystallized from a suitable organic solvent such as ether, methanol, methylene chloride, methylene chloride-methanol and the like to obtain 7-fluoro-3-ethyl-α,α-dimethyl-5-(o-chlorophenyl)-2,3-dihydro-2-oxo-1H-1,4-benzodiazepin-1-acetic acid methyl ester.

PREPARATION 10

7-Bromo-2,3-dihyro-2-oxo-5-(2-pyridyl)-1H-1,4-benzodiazepin-1-acetic acid methyl ester A mixture of 0.1 mole of 7-bromo-1,3-dihydro-5-(2-pyridyl)-2H-1,4-benzodiazepin-2-one and 0.11 mole of sodium methoxide in about 200 ml. of dimethylformamide is heated at about 95° c. for about 20 minutes. To the mixture is added a solution of 0.11 mole of methyl bromoacetate in about 200 ml. of toluene over a period of about 1 hour at about 95° C., and heating is continued for an additional period of about 6 hours. The reaction mixture is then evaporated in vacuo and the residue thus obtained is stirred with about 500 ml. of water. The resulting suspension is filtered and the solids thus obtained are crystallized from a suitable organic solvent such as ether, methanol, methylene chloride, methylene chloridemethanol and the like to obtain 7-bromo-2,3-dihydro-2-oxo-5-(2-pyridyl)-1H-1,4-benzodiazepin-1-acetic acid methyl ester.

PREPARATION 11

7-Bromo-2,3-dihydro-2-oxo-α-propyl-5-(2-pyridyl)-1H-1,4-benzodiazepin-1-acetic acid methyl ester A mixture of 0.1 mole of 7-bromo-1,3-dihydro-5-(2-pyridyl)-2H-1,4-benzodiazepin-2-one and 0.11 mole of sodium methoxide in about 200 ml. of dimethylformamide is heated at about 95° c. for about 20 minutes. To the mixture is added a solution of 0.11 mole of methyl 2-bromovalerate in about 200 ml. of toluene over a period of about 1 hour at about 95° C., and heating is continued for an additional period of about 6 hours. The reaction mixture is then evaporated in vacuo and the residue thus obtained is stirred with about 500 ml. of water. The resulting suspension is filtered and the solids thus obtained are crystallized from a suitable organic solvent such as ether, methanol, methylene chloride, methylene chloride-methanol and the like to obtain 7-bromo-2,3-dihydro-2-oxo-α-propyl-5-(2-pyridyl)-1H-1,4-benzodiazepine-1-acetic acid methyl ester.

In the manner given in the preceding preparations, other 1,3-dihydro-2H-1,4-benzodiazepin-2-ones can be reacted with the appropriate alkyl 2-haloalkanoate to provide other 2,3-dihydro-2-oxo-1H-1,4-benzodiazepin-1-acetic acid alkyl esters of formula V. For example, the following 2,3-dihydro-1H-1,4-benzodiazepin-1-acetic acid alkyl ester can be obtained:

7-bromo-2,3-dihydro-2-oxo-5-phenyl-1H-1,4-benzodiazepin-1-acetic acid methyl ester;

7-fluoro-2,3-dihydro-2-oxo-5-(2,6-difluorophenyl)-1H-1,4-benzodiazepin-1-acetic acid ethyl ester;

2,3-dihydro-7-nitro-2-oxo-5-phenyl-1H-1,4-benzodiazepin-1-acetic acid ethyl ester;

2,3-dihydro-2-oxo-α-methyl-5-(o-chlorophenyl)-1H-1,4-benzodiazepin-1-acetic acid ethyl ester;

7-bromo-2-oxo-5-(o-bromophenyl)-2,3-dihydro-1H-1,4-benzo-diazepin-1-acetic acid ethyl ester;

2-oxo-α-methyl-5-(o-fluorophenyl)-7-fluoro-2,3-dihydro-1H-1,4-benzodiazepin-1-acetic acid ethyl ester;

2oxo-α-ethyl-α,3-dimethyl-5-(o-chlorophenyl)-2,3-dihydro-1H-1,4-benzodiazepin-1-acetic acid methyl ester;

2-oxo-5-(o-chlorophenyl)-2,3-dihydro-7-(trifluoromethyl)-1H-1,4-benzodiazepin-1-acetic acid methyl ester;

2-oxo-α,α-dimethyl-5-(o-chlorophenyl)-3ethyl-2,3-dihydro-1H-1,4-benzodiazepin-1-acetic acid ethyl ester;

2-oxo-5-(o-chlorophenyl)-2,3-dihydro-7-nitro-1H-1,4-benzodiazepin-1-acetic acid propyl ester;

7-chloro-2-oxo-α,α-dimethyl-5-(o-fluorophenyl)-2,3-dihydro-1H-1,4-benzodiazepin-2-one-1-acetic acid ethyl ester;

7-bromo-2-oxo-5-(o-fluorophenyl)-2,3-dihydro-1H-1,4-benzodiazepin-1-acetic acid methyl ester;

7-fluoro-2-oxo-α,α-dimethyl-5-(o-fluorophenyl)-2,3-dihydro-1H-1,4-benzodiazepin-1-acetic acid propyl ester;

2-oxo-α-ethyl-α-methyl-5-(o-fluorophenyl)-2,3-dihydro-7-nitro-1H-1,4-benzodiazepin-1-acetic acid isopropyl ester;

2-oxo-5-(o-fluorophenyl)-2,3-dihydro-7-(trifluoromethyl)-1H-1,4-benzodiazepin-1-acetic acid methyl ester;

and the like

PREPARATION 12

7-Chloro-2,3-dihydro-5-phenyl-2-thioxo-1H-1,4-benzodiazepin-1-acetic acid methyl ester A mixture of 6.35 g. (0.0186 mole) of 7-chloro-2,3-dihydro-2-oxo-5-phenyl-1H-1,4-benzodiazepin-1-acetic acid methyl ester, 4.42 g. (0.0199 mole) of phosphorus pentasulfide and 185 ml. of pyridine is heated under reflux for about 19 hours. The pyridine is evaporated, 100 ml. of cold water is added, and the product is extracted with four 100-ml. portions of methylene chloride. The extracts are combined, washed with sodium bicarbonate solution and saturated salt solution, dried over anhydrous magnesium sulfate and evaporated to give 2.5 g. of residue. The residue thus obtained is extracted with eight 250-ml. portions of boiling ether. The extracts are combined and concentrated. On standing 2.1 g. of 7-chloro-2,3-dihydro-5-phenyl-2-thioxo-1H-1,4-benzodiazepin-1-acetic acid methyl ester of melting point 180°–182° c. crystallizes from solution; recrystallization from ether raises the melting point to 185°–187° C.

PREPARATION 13

7-Chloro-2,3-dihydro-5-phenyl-2-thioxo-1H-1,4-benzodiazepin-1-acetic acid methyl ester The procedure of Preparation 12 is repeated to the point where a residue is obtained following evaporation of the methylene chloride. The residue thus obtained is chromatographed on silica gel using 50% ethyl acetatecyclohexane to give 7-chloro-2,3-dihydro-5-phenyl-2-thioxo-1H-1,4-benzodiazepin-1-acetic acid methyl ester of melting point 188°–189° C. (from ether).

Anal. Calcd. for $C_{18}H_{15}ClN_2O_2S$: C, 60.24; H, 4.21; Cl, 9.88; N, 7.81; S, 8.94. Found: C, 60.14; H, 4.40; Cl, 9.81; N, 7.76; S, 9.06.

PREPARATION 14

7-Chloro-5-(o-chlorophenyl)-2,3-dihydro-2-thioxo-1H-1,4-benzodiazepin-1-acetic acid methyl ester A mixture of 3.8 g. (0.01 mole) of 7-chloro-5-(o-chlorophenyl)-2,3-dihydro-2-oxo-1H-1,4-benzodiazepin-1-acetic acid methyl ester, 2.3 g. (0.0105 mole) of phosphorus pentasulfide and 100 ml. of pyridine is heated under reflux for about 22 hours. The reaction mixture is evaporated and the residue thus obtained is dissolved in chloroform and 100 ml. of aqueous sodium bicarbonate solution. The organic layer is separated, washed with three 50-ml. portions of aqueous sodium bicarbonate solution and with saturated salt solution, dried over anhydrous magnesium sulfate and evaporated to remove the solvent. The residue (4.1 g.) thus obtained is dissolved in about 20 ml. of methylene chloride and chromatographed on 410 g. of silica gel. Elution with 50% ethyl acetate-methylene chloride gives 1.79 g. of 7-chloro-5-(o-chlorophenyl)-2,3-dihydro-2-thioxo-1H-1,4-benzodiazepin-1-acetic acid methyl ester. Recrystallization from ether gives 7-chloro-5-(o-chlorophenyl)-2,3-dihydro-2-thioxo-1H-1,4-benzodiazepine-1-acetic acid methyl ester of melting point 191°–192° C.; a sample, recrystallized from methanol, melts at 193°–194° C.

Anal. Calcd. for $C_{18}H_{14}Cl_2N_2O_2S$: C, 54.97; H, 3.59; Cl, 18.03; N, 7.12; S, 8.15. Found: C, 54.82; H, 3.71; Cl, 18.15; N, 6.91; S, 8.37.

PREPARATION 15

5-(o-chlorophenyl)-2,3-dihydro-2-thioxo-1H-1,4-benzodiazepin-1-acetic acid methyl ester A mixture of 7.75 g. (0.0225 mole) of 5-(o-chlorophenyl)-2,3-dihydro-2-oxo-1H-1,4-benzodiazepin-1-acetic acid methyl ester, 5.3 g. (0.0238 mole) of phosphorus pentasulfide and 200 ml. of pyridine is heated under reflux for about 23 hours. The reaction mixture is then evaporated and the residue thus obtained is dissolved in methylene chloride-water. The organic layer is separated, washed with five 100-ml. portions of saturated aqueous sodium bicarbonate solution, dried over anhydrous magnesium sulfate and evaporated to remove the solvent. The residue (7.3 g.) thus obtained is dissolved in 50 ml. of methylene chloride and chromatographed on 730 g. of silica gel. Elution with 60% ethyl acetate-cyclohexane gives 4.8 g. of product which is triturated with methanol, filtered and washed with ether to give 3.5 g. of 5-(o-chlorophenyl)-2,3-dihydro-2-thioxo-1H-1,4-benzodiazepin-1-acetic acid methyl ester; a sample after recrystallization from methanol-chloroform melts at 183°–184° C.

Anal. Calcd. for $C_{18}H_{15}ClN_2O_2S$: C, 60.24; H, 4.21; Cl, 9.88; N, 7.81; S, 8.95. Found: C, 60.11; H, 4.20; Cl, 10.06; N, 7.39; S, 9.06.

PREPARATION 16

7-Chloro-5-(2,6-difluorophenyl)-2,3-dihydro-2-thioxo-1H-1,4benzodiazepin-1-acetic acid methyl ester A mixture of 0.01 mole of 7-chloro-5-(2,6-difluorophenyl)-2,3-dihydro-2-oxo-1H-1,4-benzodiazepin-1-acetic acid methyl ester, 0.0105 mole of phosphorus pentasulfide and 100 ml. of pyridine is heated under reflux for about 24 hours. The reaction mixture is evaporated and the residue thus obtained is dissolved in methylene chloride-water. The organic layer is separated, washed with saturated sodium bicarbonate solution, dried over anhydrous magnesium sulfate and evaporated to remove the solvent. The residue thus obtained is chromatographed on silica gel and eluted to give 7-chloro-5-(2,6-difluorophenyl)-2,3-dihydro-2-thioxo-1H-1,4-benzodiazepin-1-acetic acid methyl ester.

PREPARATION 17

2,3-Dihydro-5-phenyl-2-thioxo-7-(trifluoromethyl)-1H-1,4-benzodiazepin-1-acetic acid ethyl ester A mixture of 0.01 mole of 7-trifluoromethyl-2,3dihydro-2-oxo-5-phenyl-1H-1,4-benzodiazepin-1-acetic acid ethyl ester and 0.0105 mole of phosphorus pentasulfide and 100 ml. of pyridine is heated under reflux for about 24 hours. The mixture is evaporated and the residue thus obtained is dissolved in methylene chloride-water. The organic layer is separated, washed with saturated sodium bicarbonate solution, dried over anhydrous magnesium sulfate and evaporated to remove the solvent. The residue thus obtained is chromatographed on silica gel and eluted to give 2,3-dihydro-5-phenyl-2-thioxo-7-(trifluoromethyl)-1H-1,4-benzodiazepin-1-acetic acid ethyl ester.

PREPARATION 18

7-Chloro-α,α-dimethyl-2,3-dihydro-2-thioxo-5-phenyl-1H-1,4-benzodiazepin-1-acetic acid methyl ester A mixture of 0.01 mole of 7-chloro-α,α-dimethyl-2,3-dihydro-2-oxo-5-phenyl-1H-1,4-benzodiazepin-1-acetic acid methyl ester, 0.0105 mole of phosphorus pentasulfide and 100 ml. of pyridine is heated under reflux for about 24 hours. The mixture is evaporated and the residue thus obtained is dissolved in methylene chloride-water. The organic layer is separated, washed with saturated sodium bicarbonate solution, dried over anhydrous magnesium sulfate and evaporated to remove the solvent. The residue thus obtained is chromatographed on silica gel and eluted to give 7-chloro-α,α-dimethyl-2,3-dihydro-2-thioxo-5-phenyl-1H-1,4-benzodiazepin-1-acetic acid methyl ester.

PREPARATION 19

7-Nitro-2,3-dihydro-5-(o-chlorophenyl)-2-thioxo-1H-1,4-benzodiazepin-1-acetic acid propyl ester A mixture of 0.01 mole of 7-nitro-2,3-dihydro-5-(o-chlorophenyl)-2-oxo-1H-1,4-benzodiazepin-1-acetic acid propyl ester, 0.0105 mole of phosphorus pentasulfide and 100 ml. of pyridine is heated under reflux for about 24 hours. The mixture is evaporated and the residue thus obtained is dissolved in methylene chloride-water. The organic layer is separated, washed with saturated sodium bicarbonate solution, dried over anhydrous magnesium sulfate and evaporated to remove the solvent. The residue thus obtained is chromatographed on silica gel and eluted to give 7-nitro-2,3-dihydro-5-(o-chlorophenyl)-2-thioxo-1H-1,4-benzodiazepin-1-acetic acid propyl ester.

PREPARATION 20

7-Bromo-3, α -dimethyl-5-(o-fluorophenyl)-2,3-dihydro-2-thioxo-1H-1,4-benzodiazepin-1-acetic acid methyl ester A mixture of 0.01 mole of 7-bromo-3, α -dimethyl-5-(o-fluorophenyl)-2,3-dihydro-2-oxo-1H-1,4-benzodiazepin-1-acetic acid methyl ester, 0.0105 mole of phosphorus pentasulfide and 100 ml. of pyridine is heated under reflux for about 24 hours. The mixture is evaporated and the residue thus obtained is dissolved in methylene chloride-water. The organic layer is separated, washed with saturated sodium bicarbonate solution, dried over anhydrous magnesium sulfate and evaporated to remove the solvent. The residue thus obtained is chromatographed on silica gel and eluted to give 7-bromo-3, α -dimethyl-5-(o-fluorophenyl)-2,3-dihydro-2-thioxo-1H-1,4-benzodiazepin-1-acetic acid methyl ester.

PREPARATION 21

7-Fluoro-α,α-dimethyl-3-ethyl-5-(o-chlorophenyl)-2,3-dihydro-2-thioxo-1H-1,4-benzodiazepin-1-acetic acid methyl ester A mixture of 0.01 mole of 7-fluoro-5-(o-chlorophenyl)-2,3-dihydro-α,α-dimethyl-3-ethyl-2-oxo-1H-1,4-benzodiazepin-1-acetic acid methyl ester, 0.0105 mole of phosphorus pentasulfide and 100 ml. of pyridine is heated under reflux for 24 hours. The mixture is evaporated and the residue thus obtained is dissolved in methylene chloride-water. The organic layer is separated, washed with saturated sodium bicarbonate solution, dried over anhydrous magnesium sulfate and evaporated. The residue thus obtained is chromatographed on silica gel and eluted to give 7-fluoro-α,α-dimethyl-3-ethyl-5-(o-chlorophenyl)-2,3-dihydro-2-thioxo-1H-1,4-benzodiazepin-1-acetic acid methyl ester.

PREPARATION 22

7-Bromo-2,3-dihydro-5-(2-pyridyl)-2-thioxo-1H-1,4-benzodiazepin-1-acetic acid methyl ester A mixture of 0.01 mole of 7-bromo-2,3-dihydro-5-(2-pyridyl)-2-oxo-1H-1,4-benzodiazepin-1-acetic acid methyl ester, 0.0105 mole of phosphorus pentasulfide and 100 ml. of pyridine is heated under reflux for about 24 hours. The mixture is evaporated and the residue thus obtained is dissolved in methylene chloride-water. The organic layer is separated, washed with saturated sodium bicarbonate solution, dried over anhydrous magnesium sulfate and evaporated to remove the solvent. The residue thus obtained is chromatographed on silica gel and eluted to give 7-bromo-2,3-dihydro-5-(2-pyridyl)-2-thioxo-1H-1,4-benzodiazepin-1-acetic acid methyl ester.

PREPARATION 23

7-Bromo-2,3-dihydro-α-propyl-5-(2-pyridyl)-2-thioxo-1H-1,4-benzodiazepin-1-acetic acid methyl ester A mixture of 0.01 mole of 7-bromo-2,3-dihydro-α-propyl-5-(2-pyridyl)-2-oxo-1H-1,4-benzodiazepin-1-acetic acid methyl ester, 0.0105 mole of phosphorus pentasulfide and 100 ml. of pyridine is heated under reflux for about 24 hours. The mixture is evaporated and the residue thus obtained is dissolved in methylene chloride-water. The organic layer is separated, washed with saturated sodium bicarbonate solution, dried over anhydrous magnesium sulfate and evaporated to remove the solvent. The residue thus obtained is chromatographed on silica gel and eluted to give 7-bromo-2,3-dihydro-α-propyl-5-(2-pyridyl)-2-thioxo-1H-1,4-benzodiazepin-1-acetic acid methyl ester.

In the manner given in prior Preparations 12 to 23 above, other 2,3-dihydro-2-thioxo-1H-1,4-benzodiazepin-1acetic acid alkyl esters can be obtained. Representative compounds thus obtained, include:

7-bromo-2,3-dihydro-5-phenyl-2-thioxo-1H-1,4-benzodiazepin-1-acetic acid methyl ester;
7-fluoro-2,3-dihydro-5-(2,6-difluorophenyl)-2-thioxo-1H-1,4-benzodiazepin-1-acetic acid ethyl ester;
2,3-dihydro-7-nitro-5-phenyl-2-thioxo-1H-1,4-benzodiazepin-1-acetic acid ethyl ester;
7-bromo-5-(o-bromophenyl)-2,3-dihydro-2-thioxo-1,4-benzodiazepin-1-acetic acid methyl ester;
7-fluoro-α,α-dimethyl-5-(o-fluorophenyl)-2,3-dihydro-2-thioxo-1H-1,4-benzodiazepin-1-acetic acid propyl ester;
5-(o-chlorophenyl)-2,3-dihydro-7-bromo-3-methyl-2-thioxo-1H-1,4-benzodiazepin-1-acetic acid methyl ester;
5-(o-chlorophenyl)-2,3-dihydro-2-thioxo-7-(trifluoromethyl)-1H-1,4-benzodiazepin-1-acetic acid methyl ester;
5-(o-chlorophenyl)-3-ethyl-2,3-dihydro-2-thioxo-1H-1,4-benzodiazepin-1-acetic acid methyl ester;
7-chloro-5-(o-fluorophenyl)-2,3-dihydro-2-thioxo-1H-1,4-benzodiazepin-1-acetic acid methyl ester;
7-bromo-5-(o-fluorophenyl)-2,3-dihydro-2-thioxo-1H-1,4-benzodiazepin-1-acetic acid methyl ester;
7-fluoro-5-(o-fluorophenyl)-2,3-dihydro-2-thioxo-1H-1,4-benzodiazepin-1-acetic acid methyl ester;
5-(o-fluorophenyl)-2,3-dihydro-7-nitro-2-thioxo-1H-1,4-benzodiazepin-1-acetic acid methyl ester;
5-(o-fluorophenyl)-2,3-dihydro-2thioxo-7-(trifluoromethyl)-1H-1,4-benzodiazepin-1-acetic acid methyl ester;

and the like.

PREPARATION 24

9-chloro-3,5-dihydro-7-phenyl-as-triazino-[4,3-a][1,4]benzodiazepin-2-(1H)-one

A mixture of 0.5 g. (1.4 millimoles) of 7-chloro-2,3-dihydro-5-phenyl-2-thioxo-1H-1,4-benzodiazepin-1-acetic acid methyl ester, 70 mg. (1.4 millimoles) of hydrazine hydrate and 10 ml. of methanol is refluxed for about 3.75 hours. The mixture is allowed to cool, and the crystalline precipitate, which separates, is collected on a filter; yield, 0.280 g. of 9-chloro-3,5-dihydro-7-phenyl-as-triazino[4,3-a][1,4]benzodiazepin-2-(1H)-one of melting point 267°–270° C.

Anal. Calcd. for $C_{17}H_{13}ClN_4O$: C, 62.87; H, 4.03; Cl, 10.92; N, 17.25. Found: C, 62.60; H, 3.99; Cl, 10.69; N, 17.10.

PREPARATION 25

9-Chloro-7-(o-chlorophenyl)-3,5-dihydroastriazino[4,3-a][1,4]benzodiazepin-2(1H)-one A mixture of 1.06 g. (2.7 millimoles) of 7-chloro-5-(o-chlorophenyl)-2,3-dihydro-2-thioxo-1H-1,4-benzodiazepin-1-acetic acid methyl ester, 0.14 g. (2.7 millimoles) of hydrazine hydrate and 20 ml. of methanol is refluxed for about 5 hours. The reaction mixture is then concentrated to about half of its original volume and allowed to crystallize to give on filtration 0.81 g. of 9-chloro-7-(o-chlorophenyl)-3,5-dihydro-as-triazino[4,3-a][1,4]-benzodiazepin-2(1H)-one of melting point 232°–233° C.

Anal. Calcd. for $C_{17}H_{12}Cl_2N_4O$: C, 56.84; H, 3.37; Cl, 19.74; N, 15.60. Found: C, 56.35; H, 3.33; Cl, 19.92; N, 15.59.

PREPARATION 26

9-Chloro-7-(o-chlorophenyl)-3,5-dihydroastriazino[4,3-a][1,4]benzodiazepin-2(1H)-one A mixture of 0.8 g. (2.03 millimoles) of 7-chloro-5-(o-chlorophenyl)-2,3-dihydro-2-thioxo-1H-1,4-benzodiazepin-1-acetic acid methyl ester, 94 mg. (2.03 millimoles) of hydrazine hydrate and 20 ml. of methanol is heated under reflux for about 16 hours and then allowed to stand for 2 days. The mixture is evaporated and the residue is dissolved in 10 ml. of 50% ethyl acetate-cyclohexane and 3 ml. of methylene chloride and chromatographed on 90 g. of silica gel. Elution with 5% methanol-ethyl acetate gives 0.441 g. of 9-chloro-7-(o-chlorophenyl)-3,5-dihydro-as-triazino-[4,3-a][1,4]benzodiazepin-2(1H)-one. Crystallization from ether afforded 0.255 g. of 9-chloro-7-(o-chlorophenyl)-3,5-dihydro-as-triazino[4,3-a][1,4]benzodiazepin-2(1H)-one.

PREPARATION 27

7-(o-chlorophenyl)-3,5-dihydro-as-triazino-[4,3-a][1,4]benzodiazepin-2(1H)-one

A mixture of 1.5 g. (4.34 millimoles) of 5-(o-chlorophenyl)-2,3-dihydro-2-thioxo-1H-1,4-benzodiazepin-1-acetic acid methyl ester, 0.217 g. (4.34 millimoles) of hydrazine hydrate and 20 ml. of methanol is heated under reflux for about 18.4 hours, concentrated to about half volume and allowed to stand. A yield of 1.004 g. of crystalline 7-(o-chlorophenyl)-3,5-dihydro-as-triazino[4,3-a][1,4]benzodiazepin-2(1H)-one of melting point 194°–196°C., is obtained. Recrystallization from methanol-methylene chloride raises the melting point 195°–196.5° C.

PREPARATION 28

7-(o-chlorophenyl)-3,5-dihydro-as-triazino-[4,3a][1,4]benzodiazepin-2(1H)-one A mixture of 1.55 g. (4.34 millimoles) of 5-(o-chlorophenyl)-2,3-dihydro-2-thioxo-1H-1,4-benzodiazepin-1-acetic acid methyl ester, 0.199 g. (4.34 millimoles) of hydrazine and 20 ml. of methanol is heated under reflux for about 18.5 hours. The reaction mixture is allowed to crystallize to give 0.303 g. of unreacted starting material which separates and is removed by filtration. The filtrate is evaporated and the residue thus obtained is dissolved in about 5 ml. of methylene chloride and chromatographed on 110 g. of silica gel. Elution with ethyl acetate gives 7-(o-chlorophenyl)-3,5-dihydro-as-triazino[4,3-a][1,4]-benzodiazepin-2(1H)-one.

PREPARATION 29

9-Chloro-3,5-dihydro-7-phenyl-as-triazino-[4,3-a][1,4]benzodiazepin-2(1H)-one

A mixture of 1.1 g. (3.08 millimoles) of 7-chloro-2,3-dihydro-5-phenyl-2-thioxo-1H-1,4-benzodiazepin-1-acetic acid methyl ester, 0.142 g. (3.08 millimoles) of hydrazine hydrate and 20 ml. of methanol is heated under reflux for about 20 hours. The reaction mixture is evaporated and the residue thus obtained is chromatographed on 240 g. of silica gel. Elution with ethyl acetate gives 0.523 g. of 9-chloro-3,5-dihydro-7-phenyl-as-triazino[4,3-a][1,4]benzodiazepin-2(1H)-one, which is recrystallized from ether to give 9-chloro-3,5-dihydro-7-phenyl-as-triazino[4,3-a][1,4]benzo-diazepin-2(1H)-one.

PREPARATION 30

9-Chloro-7-(2,6-difluorophenyl)-3,5-dihydroas-triazino[4,3-a][1,4]benzodiazepin-2(1H)-one A mixture of 3.0 millimoles of 7-chloro-2,3-dihydro-5-(2,6-difluorophenyl)-2-thioxo-1H-1,4-benzodiazepin-1-acetic acid methyl ester, 3.0 millimoles of hydrazine hydrate and 20 ml. of methanol is heated under reflux until the reaction is complete. The reaction mixture is then evaporated to dryness, and the residue thus obtained is chromatographed on silica gel and eluted therefrom to give 9-chloro-7-(2,6-difluorophenyl)-3,5-dihydro-astriazino[4,3-a][1,4]benzodiazepin-2(1H)-one.

PREPARATION 31

3,5-Dihydro-7-phenyl-9-(trifluoromethyl)-as-triazino[4,3-a][1,4]benzodiazepin-2(1H)-one A mixture of 3-millimoles of 2,3-dihydro-5-phenyl-2-thioxo-7-(trifluoromethyl)-1H-1,4-benzodiazepin-1-acetic acid ethyl ester, 3.0 millimoles of hydrazine hydrate and 20 ml. of methanol is heated under reflux until the reaction is complete. The reaction mixture is then evaporated to dryness, and the residue thus obtained is chromatographed on silica gel and eluted therefrom to give 3,5-dihydro-7-phenyl-9-(trifluoromethyl)-as-triazino-[4,3-a][1,4]benzodiazepin-2(1H)-one.

PREPARATION 32

9-Nitro-3,5-dihydro-7-(o-chlorophenyl)-as-triazino[4,3-a][1,4]benzodiazepin-2(1H)-one A mixture of 3.0 millimoles of 7-nitro-2,3-dihydro-5-(o-chlorophenyl)-2-thioxo-1H-1,4-benzodiazepin-1-acetic acid methyl ester, 3.0 millimoles of hydrazine hydrate and 20 ml. of methanol is heated under reflux until the reaction is complete. The reaction mixture is then evaporated to dryness, and the residue thus obtained is chromatographed on silica gel and eluted therefrom to give 9-nitro-3,5-dihydro-7-(o-chlorophenyl)-as-triazino-[4,3-a][1,4]benzodiazepin-2(1H)-one.

PREPARATION 33

9-Fluoro-7-(o-fluorophenyl)-3,5-dihydro-as-triazino[4,3-a][1,4]benzodiazepine-2(1H)-one A mixture of 3.0 millimoles of 7-fluoro-2,3-dihydro-5-(o-fluorophenyl)-2-thioxo-1H-1,4-benzodiazepin-1-acetic acid methyl ester, 3.0 millimoles of hydrazine hydrate, and 20 ml. of methanol is heated under reflux until the reaction is complete. The solvent is then removed from the reaction mixture by evaporation and the residue thus obtained is chromatographed on silica gel and eluted therefrom to give 9-fluoro-7-(o-fluorophenyl)-3,5-dihydro-as-triazino[4,3-a][1,4]benzodiazepin-2(1H)-one.

PREPARATION 34

9-Bromo-3,5-dihydro-7-(m-fluorophenyl)-1,1,5-trimethyl-as-triazino[4,3-a][1,4]benzodiazepin-2(1H)-one A mixture of 3.0 millimoles of 7-bromo-2,3-dihydro-$\alpha,\alpha$,3-trimethyl-5-(m-fluorophenyl)-2-thioxo-1H-1,4-benzodiazepin-1-acetic acid methyl ester, 3.0 millimoles of hydrazine hydrate and 20 ml. of methanol is heated under reflux until the reaction is complete. The solvent is then removed from the reaction mixture by evaporation and the residue thus obtained is chromotographed on silica gel and eluted therefrom to give 9-bromo-3,5-dihydro-7-(m-fluorophenyl)-1,1,5-trimethyl-as-triazino[4,3-a][1,4]-benzodiazepin-2(1H)-one.

PREPARATION 35

9-Bromo-7-(o-fluorophenyl)-1,1,5-trimethyl-as-triazino[4,3-a][1,4]benzodiazepin-2(1H)-one A mixture of 3.0 millimoles of 7-bromo-5-(o-fluorophenyl)-2,3-dihydro$\alpha,\alpha$-3-trimethyl-2-thioxo-1H-1,4-benzodiazepin-1-acetic acid methyl ester, 3.0 millimoles of hydrazine hydrate and 20 ml. of methanol is heated under reflux until the reaction is complete. The solvent is then removed from the reaction mixture by evaporation and the residue thus obtained is chromatographed on silica gel and eluted therefrom to give 9-bromo-7-(o-fluorophenyl)-1,1,5-trimethyl-3,5-dihydro-as-triazino[4,3-a][1,4]benzodiazepin-2(1H)-one.

PREPARATION 36

9-Bromo-3,5-dihydro-7-(2-pyridyl)-as-triazino[-pyridyl)-as-triazino[4,3-a][1,4]benzodiazepin-2(1H)-one A mixture of 3.0 millimoles of 7-bromo-2,3-dihydro-5-(2-pyridyl)-2-thioxo-1H-1,4-benzodiazepin-1-acetic acid methyl ester, 3.0 millimoles of hydrazine hydrate and 20 ml. of methanol is heated under reflux until the reaction is complete. The solvent is then removed from the reaction mixture by evaporation and the residue thus obtained is chromatographed on silica gel and eluted therefrom to give 9-bromo-3,5-dihydro-7-(2-pyridyl)-as-triazino[4,3-a]-[1,4]benzodiazepin-2(1H)-one.

PREPARATION 37

9-Bromo-5-ethyl-3,5-dihydro-1-propyl-7-(2-pyridyl)-as-triazino[4,3-a][1,4]benzodiazepin-2(1H)-one A mixture of 3.0 millimoles of 7-bromo-3-ethyl-2,3-dihydro-α-propyl-5-(2-pyridyl)-2-thioxo-1H-1,4-benzodiazepine-1-acetic acid methyl ester, 3.0 millimoles of hydrazine hydrate and 20 ml. of methanol is heated under reflux until the reaction is complete. The solvent is then removed from the reaction mixture by evaporation and the residue thus obtained is chromatographed on silica gel and eluted therefrom to give 9-bromo-5-ethyl-3,5-dihydro-1-propyl-7-(2-pyridyl)-as-triazino[4,3-a][1,4]benzodiazepin-2(1H)-one.

In the manner given in the preceding Preparations, other 2,3-dihydro-2-thioxo-1H-1,4-benzodiazepin-1-acetic acid alkyl esters can be condensed with hydrazine hydrate to give other 3,5-dihydro-as-triazino-[4,3-a][1,4]benzodiazepin-2(1H)-ones. Representative starting compounds thus obtained, include:

9-bromo-3,5-dihydro-7-phenyl-as-triazino[4,3-a][1,4]-benzodiazepin-2(1H)-one;
9-fluoro-3,5-dihydro-7-phenyl-as-triazino[4,3-a][1,4]-benzodiazepin-2(1H)-one;
3,5-dihydro-9-nitro-7-phenyl-as-triazino[4,3-a][1,4]-benzodiazepin-2(1H)-one;
3,5-dihydro-7-phenyl-10-(trifluoromethyl)-as-triazino-[4,3-a][1,4]benzodiazepin-2(1H)-one;
3,5-dihydro-1,1-diethyl-8-chloro-7-phenyl-as-triazino-[4,3-a][1,4]benzodiazepin-2(1H)-one;
9-bromo-7-(o-bromophenyl)-3,5-dihydro-as-triazino[4,3-a]-[1,4]benzodiazepin-2(1H)-one;
7-(o-chlorophenyl)-9-fluoro-1,1,5-trimethyl-3,5-dihydro-as-triazino[4,3-a][1,4]benzodiazepin-2(1H)-one;
7-(o-chlorophenyl)-9-fluoro-3,5-dihydro-as-triazino[4,3-a]-[1,4]benzodiazepin-2(1H)-one;
7-(o-chlorophenyl)-3,5-dihydro-9-fluoro-5-methyl-as-triazino[4,3-a][1,4]benzodiazepin-2(1H)-one;
7-(o-chlorophenyl)-3,5-dihydro-9-(trifluoromethyl)-as-triazino[4,3-a][1,4]benzodiazepin-2(1H)-one;
7-(o-chlorophenyl)-5-ethyl-3,5-dihydro-as-triazino[4,3-a]-[1,4]benzodiazepin-2(1H)-one;
7-(o-chlorophenyl)-3,5-dihydro-9-bromo-as-triazino[4,3-a]-[1,4]benzodiazepin-2(1H)-one;
9-chloro-7-(o-fluorophenyl)-3,5-dihydro-as-triazino[4,3-a]-[1,4]benzodiazepin-2(1H)-one;
9-bromo-7-(o-fluorophenyl)-3,5-dihydro-as-triazino[4,3-a]-[1,4]benzodiazepin-2(1H)-one;
7-(o-fluorophenyl)-3,5-dihydro-9-nitro-as-triazino[4,3-a]-[1,4]benzodiazepin-2(1H)-one;
7-(o-fluorophenyl)-3,5-dihydro-9-(trifluoromethyl)-as-triazino[4,3-a][1,4]benzodiazepin-2(1H)-one;
7-(p-chlorophenyl)-9-fluoro-3,5-dihydro-as-triazino[4,3-a][1,4]benzodiazepin-2(1H)-one;
7-(p-fluorophenyl)-3,5-dihydro-9-nitro-as-triazino[4,3-a]-[1,4]benzodiazepin-2(1H)-one;

and the like.

EXAMPLE 1

9-Chloro-7-(o-chlorophenyl)-3-[(dimethylamino)-methyl]-3,5-dihydro-as-triazino[4,3-a][1,4]benzodiazepin-2(1H)-one A. Preparation of dimethylmethyleneammonium chloride according to Böhme et al., Ber., 93, 1305 (1960); Arch. Pharm. 305, 612 (1972).

Acetyl chloride (distilled, 0.71 ml. 0.01 mole) is added dropwise during 2 minutes to a stirred solution of N, N, N', N'-tetramethyldiaminomethane (1.02 g; 0.01 mole) in 30 ml. of ether. The resulting suspension is stirred for 25 minutes and filtered. The colorless solid is washed with ether (2 × 25 ml.) and used directly in the next step.

B 9-Chloro-7-(o-chlorophenyl)-3-[(dimethylamino)-methyl]-3,5-dihydro-as-triazino-[4,3-a][1,4]benzodiazepin-2(1H)-one Solid 9-chloro-7-(o-chlorophenyl)-3,5-dihydro-as-triazino[4,3-a][1,4]benzodiazepin-2(1H)-one (3.59 g; 0.01 mole) is added to a suspension of sodium hydride (57% dispension in mineral oil, 421 mg. 0.01 mole washed with 3 × 10 ml. of petroleum-ether boiling range 30°–60° C.) In 50 ml. of dimethylforamanide, and the mixture is heated on the steambath for 1 hour. The resulting brown solution is cooled to circa 40° C., dimethylmethyleneammonium chloride (freshy prepared as above) is added. The mixture is heated on the steambath or 20 hours and evaporated. The residue is dissolved in chloroform-water, the aqueous layer is extracted once with chloroform and the combined organic solution is washed twice with water, once with saturated salt solution, dried over anhydrous magnesium sulfate and evaporated. The crude product (4.4 g) shows an nmr spectrum (CDCl₃) which compares well with the nmr of the pure product obtained below.

The crude product (4.4 g) is extracted with 2 × 200 ml. of boiling petroleum-ether (30°–60°). Residue A amounts to 4 g. The extract is concentrated to 15 ml. and is allowed to crystallize to give 50 mg. of 9-chloro-7-(o-chlorophenyl)-3-[(dimethylamino)methyl]-3,5-dihydro-as-triazino[4,3-a][1,4]benzodiazepin-2(1H)-one of melting point 141°–143° C. Recrystallization from Skellysolve B hexanes with a drop of ether gives 35 mg. of the pure product of melting point 142°–143° C.

Residue A is extracted with 4 × 100 ml. of boiling ether (residue: 0.45 g), the extract is concentrated and seeded to give 1.416 g. (solid B) melting point 122°–129° (cloudy) and filtrate B. Solid B is extracted with 8 × 200 ml. of boiling Skellysolve B hexanes (residue: 0.31 g), concentrated to cloudiness and allowed to crystallize; pale yellow prisms, 0.578 g of melting point 140°–141° C. are obtained. Second crop: 0.120 g. of the same melting point. ether cloudiness The ther filtrate B is evaporated, the residue is extracted with 8 portions of 200 ml. of Skellysolve B hexanes, which are combined, filtered to separate the insoluble, and the filtrate is concentrated to cludiness, clarified with ether and seeded to give 0.261 g, melting point 140°–141° C. (Yield: 24% 0.994 g).

Anal. Calcd. for $C_{20}H_{19}Cl_2N_5O$: C, 57.70; H, 4.60; Cl, 17.03; N, 16.82. Found: C, 57.80; H, 4.80; Cl, 17.03; N, 17.07.

EXAMPLE 2

9-Chloro-7-phenyl-3-[(dimethylamino)methyl]-3,5-dihydro-as-triazino[4,3-a][1,4]benzodiazepin-2(1H)-one In the manner given in Example 1, 9-chloro-7-phenyl-3,5-dihydro-as-triazino[4,3-a][1,4]benzodiazepin-2(1H)-one is treated with freshly prepared dimethylmethyleneammonium chloride to give 9-chloro-7-phenyl-3-[(dimethyl-amino)methyl]-3,5-dihydro-as-triazino[4,3-a][1,4]benzodiazepin-2(1H)-one.

EXAMPLE 3

9-Chloro-7-(2,6-difluorophenyl)-3-[(dimethyl-amino)methyl]-3,5-dihydro-as-triazino[4,3-a][1,4]benzodiazepin-2(1H)-one In the manner given in Example 1, 9-chloro-7-(2,6-difluorophenyl)-3,5-dihydro-as-triazino[4,3-a][1,4]benzodiazepin-2(1H)-one is treated with freshly prepared dimethylmethyleneammonium chloride to give 9-chloro-7-(2,6-difluorophenyl)-3-[(dimethylamino)methyl]-3,5-dihydro-as-triazino[4,3-a][1,4]benzodiazepin-2(1H)-one.

EXAMPLE 4

9-(Trifluoromethyl)-7-phenyl-3-[(dimethylamino)methyl]-3,5-dihydro-as-triazino[4,3-a][1,4]benzodiazepin-2(1H)-one In the manner given in Example 1, 9-(trifluoromethyl)-7-phenyl-3,5-dihydro-as-triazino[4,3-a][1,4]benzodiazepin-2(1H)-one is treated with freshly prepared dimethylmethyleneammonium chloride to give 9-(trifluoromethyl)-7-phenyl-3-[(dimethylamino)methyl]-3,5-dihydro-as-triazino[4,3-a][1,4]-benzodiazepin-2(1H)-one.

EXAMPLE 5

9-Nitro-7-(o-chlorophenyl)-3-[(dimethylamino)methyl]-3,5-dihydro-as-triazino[4,3-a][1,4]benzodiazepin-2(1H)-one In the manner given in Example 1, 9-nitro-7-(o-chlorophenyl)-3,5-dihydro-as-triazino[4,3-a][1,4]benzodiazepin-2(1H)-one is treated with freshly prepared dimethylmethyleneammonium chloride to give 9-nitro-7-(o-chlorophenyl)-3-[(dimethylamino)methyl]-3,5-dihydro-as-triazino[4,3-a][1,4]-benzodiazepin-2(1H)-one.

EXAMPLE 6

9-Fluoro-7-(o-fluorophenyl)-3-[(dimethylamino)methyl]-3,5-dihydro-as-triazino[4,3-a][1,4]benzodiazepin-2(1H)-one In the manner given in Example 1, 9-fluoro-7-(o-fluorophenyl)-3,5-dihydro-as-triazino[4,3-a][1,4]benzodiazepin-2(1H)-one is treated with freshly prepared dimethylmethyleneammonium chloride to give 9-fluoro-7-(o-fluorophenyl)-3-[(dimethylamino)methyl]-3,5-dihydro-as-triazino[4,3-a]-[1,4]benzodiazepin-2(1H)-one.

EXAMPLE 7

9-Bromo-7-(o-fluorophenyl)-3-[(dimethylamino)methyl]-3,5-dihydro-as-triazino[4,3-a][1,4]benzodiazepin-2(1H)-one In the manner given in Example 1, 9-bromo-7-(o-fluorophenyl)-3,5-dihydro-as-triazino[4,3-a][1,4]benzodiazepin-2(1H)-one is treated with freshly prepared dimethylmethyleneammonium chloride to give 9-bromo-7-(o-fluorophenyl)-3-[(dimethylamino)methyl]-3,5-dihydro-as-triazino[4,3-a][1,4]benzodiazepin-2(1H)-one.

EXAMPLE 8

9-Bromo-7-(2pyridyl)-3-[ ]dimethylamino)methyl]-3,5-dihydro-as-triazino[4,3-a][1,4]benzodiazepin-2(1H)-one In the manner given in Example 1, 9-bromo-7-(2-pyridyl)-3,5-dihydro-as-triazino[4,3-a][1,4]benzodiazepin-2(1H)-one is treated with freshly prepared dimethylmethyleneammonium chloride to give 9-bromo-7-(2-pyridyl)13-[(dimethylamino)methyl]-3,5-dihydro-as-triazino[4,3-a][1,4]-benzodiazepin-2(1H)-one.

EXAMPLE 9

N-methyl-N-ethylmethyleneammonium chloride

To N, N'-dimethyl-N,N'-diethyldiaminomethane in ether is added acetyl chloride in equal molar quantity to provide a solution of N-methyl-N-ethylmethyleneammonium chloride, used in Example 10.

EXAMPLE 10

9-Chloro-7-(o-chlorophenyl)-3-[(ethylmethylamino)methyl]-3,5-dihydro-as-triazino[4,3-a][1,4]benzodiazepin-2(1H)-one In the manner given in Example 1, 9-chloro-7-(o-chlorophenyl)-3,5-dihydro-as-triazino[4,3-a][1,4]benzodiazepin-2(1H)-one is treated with freshly prepared N-methyl-N-ethylmethyleneammonium chloride to give 9-chloro-3-[(methylethylamino)methyl]-7-(o-chlorophenyl)-3,5-dihydro-as-triazino[4,3-a][1,4]benzodiazepin-2(1H)-one.

EXAMPLE 11

Diethylmethyleneammonium chloride

To N,N,N',N'-tetraethyldiaminomethane in ether is added an equimolecular amount of acetyl chloride. After stirring for ½ hour, the colorless solid which separates is recovered by filtration providing diethylmethyleneammonium chloride which is used in the next example.

EXAMPLE 12

9-Chloro-7-(0-chlorophenyl)-3-[(diethylamino)methyl]-3,5-dihydro-as-triazino[4,3-a][1,4]benzodiazepin-2(1H)-one In the manner given in Example 1, 9-Chloro-7-(o-chlorophenyl)-3,5-dihydro-as-triazino[4,3-a][1,4]benz9diazepin-2(1H)-one is treated with freshly prepared diethylmethyleneammonium chloride to give 9-chloro-7-(o-chlorophenyl)-3-[(diethylamino)methyl]-3,5-dihydro-as-triazino[4,3- a][1,4]benzodiazepine-2(1H)-one.

EXAMPLE 13

Dipropylmethyleneammonium chloride

To N,N,N',N'-tetrapropyldiaminomethane in ether is added an equimolecular amount of acetyl chloride. After stirring for ½ hour the colorless solid which separates is recovered by filtration providing dipropylmethyleneammonium chloride which is used in the next example.

EXAMPLE 14

9-(Trifluoromethyl)-7-phenyl-3-[(dipropylamino)methyl]-3,5-dihydro-as-triazino[4,3-a][1,4]benzodiazepine-2(1H)-one In the manner given in Example 1, 9-(trifluoromethyl)-7-phenyl-3,5-dihydro-as-triazino[4,3-a][1,4]benzodiazepin-2(1H)-one is treated with freshly prepared dipropylmethyleneammonium chloride to give 9-(trifluoromethyl)-7-phenyl-3-[(dipropylamino)methyl]-3,5-dihydro-as-triazino-[4,3-a][1,4]benzodiazepine-2(1H)-one.

EXAMPLE 15

1-methylenepiperidinium chloride

To dipiperidinomethane in ether is added an equimolecular amount of acetyl chloride. After stirring for ½ hour the colorless solid which separates is recovered by filtration providing 1-methylenepiperidinium chloride which is used in the next example.

EXAMPLE 16

9-Fluoro-7-(o-fluorophenyl)-3-(piperidinomethyl)-3,5-dihydro-as-triazino[4,3-a][1,4]benzodiazepine-2(1H)-one In the manner given in Example 1, 9-fluoro-7-(o-fluorophenyl)-3,5-dihydro-as-triazino[4,3-a][1,4]benzodiazepin-2(1H)-one is treated with freshly prepared 1-methylenepiperidinium chloride to give 9-fluoro-7-(o-fluorophenyl)-3-(piperidinomethyl)-3,5-dihydro-as-triazino[4,3-a][1,4]benzodiazepine-2(1H)-one.

EXAMPLE 17

9-Chloro-7-phenyl-3-(piperidinomethyl)-3,5-dihydro-as-triazino[4,3-a][1,4]benzodiazepin-2(1H)-one In the manner given in Example 1, 9-chloro-7-phenyl-3,5-dihydro-as-triazino[4,3-a][1,4]benzodiazepin-2(1H)-one is treated with freshly prepared 1-methylenepiperidinium chloride to give 9-chloro-7-phenyl-3-(piperidinomethyl)3,5-dihydro-as-triazino[4,3-a][1,4]benzodiazepin-2(1H)-one.

EXAMPLE 18

9-Chloro-7-(o-chlorophenyl)-3-(piperidinomethyl)-3,5-dihydro-as-triazino[4,3-a][1,4]benzodiazepin-2(1H)-one In the manner given in Examaple 1, 9-chloro-7-(o-chlorophenyl)-3,5-dihydro-as-triazino[4,3-a][1,4]benzodiazepin-2(1H)-one is treated with freshly prepared 1-methylenepiperidinium chloride to give 9-chloro-7-(o-chlorophenyl)-3-(piperidinomethyl)-3,5-dihydro-as-triazino-[4,3-a][1,4]benzodiazepin-2(1H)-one.

EXAMPLE 19

9-Bromo-7-(2-pyridyl)-3-(piperidinomethyl)-3,5-dihydro-as-triazino[4,3-a][1,4]benzodiazepin-2(1H)-one In the manner given in Example 1, 9-bromo-7-(2-pyridyl)-3,5-dihydro-as-triazino[4,3-a][1,4]benzodiazepin-2(1 H)-one is treated with freshly prepared 1-methylenepiperidinium chloride to give 9-bromo-7-(2-pyridyl)-3-(piperidinomethyl)-3,5-dihydro-as-triazino[4,3-a][1,4]-benzodiazepin-2(1H)-one.

EXAMPLE 20

4-methylenemorpholinium chloride

To dimorpholinomethane in ether is added an equimolecular amount of acetly chloride. After stirring for ½ hour the colorless solid which separates is recovered by filtration providing 4-methylenemorpholinium chloride which is used in the next example.

EXAMPLE 21

9-Nitro-7-(o-chlorophenyl)-3-(morpholinomethyl)-3,5-dihydro-as-triazino[4,3-a][1,4]benzodiazepine-2(1H)-one In the manner given in Example 1, 9-nitro-7-(o-chlorophenyl)-3,5-dihydro-as-triazino[4,3-a][1,4]benzodiazepin-2(1H)-one is treated with freshly prepared 4-methylenemorpholinium chloride to give 9-nitro-7-(o-chlorophenyl)-3-(morpholinomethyl)-3,5-dihydro-as-triazino[4,3-a][1,4]-benzodiazepine-2(1H)-one.

EXAMPLE 22

1-Methylenepyrrolidinium chloride

To dipyrrolidinomethane in ether is added an equimolecular amount of acetyl chloride. After stirring for ½ hour, the colorless solid which separates is recovered by filtration providing 1-methylenepyrrolidinium chloride which is used in the next example.

EXAMPLE 23

9-Bromo-1,1,5-trimethyl-7-(o-fluorophenyl)-3-(pyrrolidinomethyl)-3,5-dihydro-as-triazino[4,3-a][1,4]-benzodiazepine-2(1H)-one In the manner given in Example 1, 9-bromo-1,1,5-trimethyl-7-(o-fluorophenyl)-3,5-dihydro-as-triazino-[4,3-a][1,4]benzodiazepin-2(1H)-one is treated with freshly prepared 1-methylenepyrrolidinium chloride to give 9-bromo-1,1,5-trimethyl-7-(o-fluorophenyl)-3-(pyrrolidinomethyl)-3,5-dihydro-as-triazino[4,3-a][1,4]benzodiazepin-2(1H)-one.

EXAMPLE 24

4-Methyl-1-methylenepiperazinium chloride to bis(4-methylpiperazino)methane in ether is added an equimolecular amount of acetyl chloride. After stirring for ½ hour, the colorless solid which separates is recovered by filtration providing 4-methyl-1-methylenepiperazinium chloride which is used in the next example.

EXAMPLE 25

9-Chloro-7-(2,6-dilfuorophenyl)-3-[(methylpiperazino)methyl]-3,5-dihydro-as-triazino[4,3-a][1,4]-benzodiazepin-2(1H)-one In the manner given in Example 1, 9-chloro-7-(2,6-difluorophenyl)-3,5-dihydro-as-triazino[4,3-a][1,4]- benzodiazepin-2(1H)-one is treated with freshly prepared 4-methyl-1-methylenepiperazinium chloride to give 9-chloro-7-(2,6-difluorophenyl)-3-[(4-methylpiperazino)methyl]-3,5-dihydro-as-triazino[4,3-a][1,4]benzodiazepine-2(1H)-one.

EXAMPLE 26

Diisopropylmethyleneammonium chloride

To N,N,N',N'-tetraisopropyldiaminomethane in ether is added an equimolecular amount of acetyl chloride. After stirring for ½ hour, the colorless solid which separates is recovered by filtration providing diisopropylmethyleneammonium chloride which is used in the next example.

EXAMPLE 27

9-Chloro-7-(o-chlorophenyl)-3-[(diisopropylamino)-methyl]-3,5-dihydro-as-triazino[4,3-a][1,4]benzodiazepin-2(1H)-one In the manner given in Example 1, 9-chloro-7-(o-chlorophenyl)-3,5-dihydro-as-triazino[4,3-A][1,4]benzodiazepin-2(1H)-one is treated with freshly prepared diisopropylmethyleneammonium chloride to give 9-chloro-7-(o-chlorophenyl)-3-[(diisopropylamino)methyl]-3,5-dihydro-as-triazino[4,3-a][1,4]benzodiazepin-2(1H)-one.

In the same manner given in the preceding examples other 3-[(substituted amino)methyl]-3,5-dihydro-7-substituted-as-triazino[4,3-a][1,4]benzodiazepin-2(1H)-ones are prepared. Representative compounds, thus obtained, include:

9-chloro-7-phenyl-3-(morpholinomethyl)-3,5-dihydro-as-triazino[4,3-a][1,4]benzodiazepin-2(1H)-one;
7-(o-chlorophenyl)-3-[(dimethylamino)methyl]-3,5-dihydro-as-triazino[4,3-a][1,4]benzodiazepin-2(1H)-one;
9-nitro-7-phenyl-3-[(diethylamino)methyl]-3,5-dihydro-as-triazino[4,3-a][1,4]benzodiazepin-2(1H)-one;
9-nitro-7-(o-chlorophenyl)-3-[(dipropylamino)methyl]-3,5-dihydro-as-triazino[4,3-a][1,4]benzodiazepin-2(1H)-one;
9-chloro-7-(o-fluorophenyl)-1,1,5-trimethyl-3-(piperidinomethyl)-3,5-dihydro-as-triazino[4,3-a][1,4]benzodiazepin-2(1H)-one;
9-trifluoromethyl-7-phenyl-5-methyl-3-(pyrrolidinomethyl)-3,5-dihydro-as-triazino[4,3-a][1,4]benzodiazepin-2(1H)-one;
9-trifluoromethyl-7-(o-fluorophenyl)-3-[(diethylamino)-methyl]-3,5-dihydro-as-triazino[4,3-a][1,4]benzodiazepin-2(1H)-one;
9-fluoro-7-(o-chlorophenyl)-5-methyl-3-(morpholinomethyl)-3,5-dihydro-as-triazino[4,3-a][1,4]benzodiazepin-2(1H)-one;
9-bromo-7-(o-fluorophenyl)-3-[(4-methylpiperazino)-methyl)]-3,5-dihydro-as-triazino[4,3-a][1,4]benzodiazepin-2(1H)-one;
9-bromo-7-phenyl-3-(pyrrolidinomethyl)-3,5-dihydro-as-triazino[4,3-a][1,4]benzodiazepin-2(1H)-one;
9-bromo-7-(o-bromophenyl)-3-[(dimethylamino)methyl]-3,5-dihydro-as-triazino[4,3-a][1,4]benzodiazepin-2(1H)-one;
8-chloro-7-phenyl-1,1-diethyl-3-[(dimethylamino)methyl]-3,5-dihydro-as-triazino[4,3-a][1,4]benzodiazepin-2(1H)-one;
9-fluoro-7-(o-chlorophenyl)-1,1-dimethyl-3-[(dimethylamino)methyl]-3,5-dihydro-as-triazino[4,3-a][1,4]benzodiazepin-2(1H)-one;
9-(trifluoromethyl)-7-(o-chhlorophenyl)-5-methyl-3-[(diethylamino)methyl]-3,5-dihydro-as-triazino[4,3-a][1,4]benzodiazepin-2(1H)-one;
9-bromo-1,1-dimethyl-3-[(dimethylamino)methyl]-7-(2-pyridyl)-3,5-dihydro-as-triazino[4,3-a][1,4]benzodiazepin-2(1H)-one;
and the like.

I claim:

1. A compound of the formula II

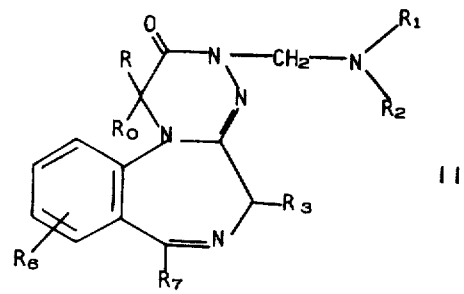

wherein R, $R_0$, and $R_3$ are hydrogen or alkyl of 1 to 3 carbon atoms, inclusive; wherein $R_1$ and $R_2$ are alkyl defined as above, or the group

together is pyrrolidino, piperidino, morpholino and N-methylpiperazino; wherein $R_7$ is 2-pyridyl or a phenyl radical of the formula

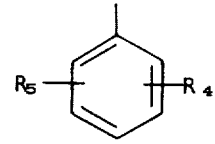

wherein $R_4$ is hydrogen, fluoro, or chloro; wherein $R_5$ is hydrogen or fluoro, with the proviso that $R_5$ is not fluoro, when $R_4$ is chloro; and wherein $R_6$ is hydrogen, chloro, fluoro, bromo, trifluoromethyl, or nitro.

2. A compound according to claim 1, wherein R, $R_0$, and $R_3$ are hydrogen; $R_1$ and $R_2$ are methyl; $R_6$ is 9-bromo; $R_7$ is 2-pyridyl; and the compound is therefore 9-bromo-7-(2-pyridyl)-3-[(dimethylamino)methyl]-3,5-dihydro-as-triazino[4,3-a][1,4]benzodiazepin-2(1H)-one.

3. A compound according to claim 1 of the formula IIA:

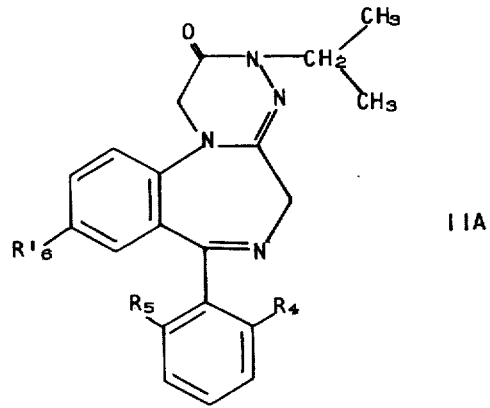

wherein $R_4$ is hydrogen, chloro, or fluoro; wherein $R_5$ is hydrogen or fluoro, with the proviso that $R_5$ is not fluoro, when $R_4$ is chloro; and wheein $R'_6$ is hydrogen, chloro, fluoro, trifluoromethyl, or nitro.

4. A compound according to claim 1 of the formula IIB:

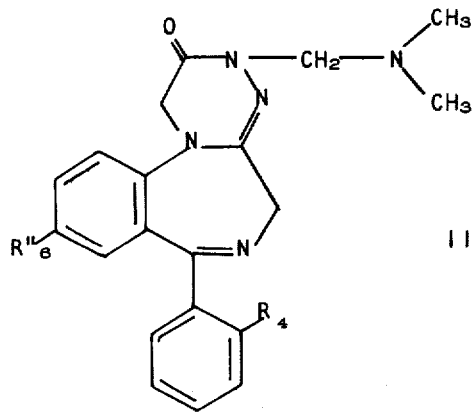

$R''_6$ is chloro, trifluoromethyl or fluoro; and $R_4$ is hydrogen, chloro or fluoro.

5. A compound according to claim 4, wherein $R_4$ and $R''_6$ are chlorine and the compound is therefore 9-chloro-7-(o-chlorophenyl)-3-[(dimethylamino)methyl]-3,5-dihydro-as-triazino[4,3-a][1,4]benzodiazepin-2(1H)-one.

6. A compound according to claim 4, wherein $R_4$ is hydrogen, $R''_6$ is chlorine and the compound is therefore 9-chloro-7-phenyl-3-[(dimethylamino)methyl]-3,5-dihydro-as-triazino[4,3-a][1,4]benzodiazepin-2(1H)-one.

7. A compound according to claim 3, wherein $R_4$ and $R_5$ are fluoro and $R'_6$ is chloro and the compound is therefore 9-chloro-7-(2,6-difluorophenyl)-3-[(dimethylamino)methyl]-3,5-dihydro-as-triazino[4,3-a][1,49 benzodiazepin-2(1H)-one.

8. A compound according to claim 3, wherein $R_4$ and $R_5$ are hydrogen, $R'_6$ is trifluoromethyl and the compound is therefore 9-(trifluoromethyl)-7-phenyl-3-[(dimethylamino)-methyl]-3,5-dihydro-as-triazino[4,3-a][1,4]benzodiazepin-2(1H)-one.

9. A compound according to claim 3, wherein $R_4$ is chlorine, $R_5$ is hydrogen, $R'_6$ is nitro, and the compound is therefore 9-nitro-7-(o-chlorophenyl)-3-[(dimethylamino)-methyl]-3,5-dihydro-as-triazino[4,3-a][1,4]benzodiazepin-2(1H)-one.

10. A compound according to claim 4, wherein $R_4$ is fluoro, $R''_6$ is fluoro and the compound is therefore 9-fluoro-7-(o-fluorophenyl)-3-[(dimethylamino)methyl]-3,5-dihydro-as-triazino[4,3-a][1,4]benzodiazepin-2(1H)-one.

11. A compound according to claim 1 wherein

is piperidino, R, $R_0$, and $R_3$ are hydrogen, $R_7$ is a phenyl radical of the formula

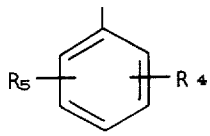

in which $R_4$ is o-chloro and $R_5$ is hydrogen, $B_6$ is 9-chloro, and the compound is therefore 9-chloro-3-(piperidinomethyl)-7-(o-chlorophenyl)-3,5-dihydro-as-triazino[4,3-a][1,4]-benzodiazepin-2(1H)-one.

12. A process for the production of a compound of the formula II:

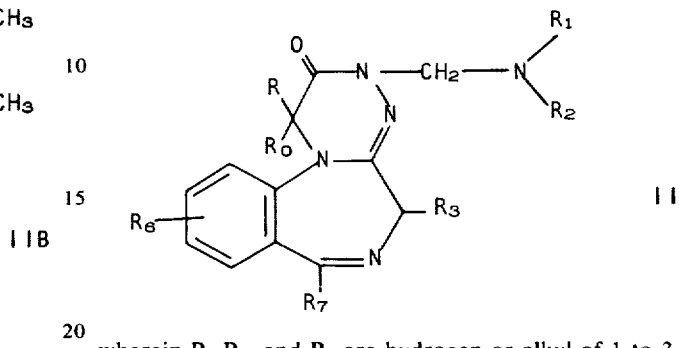

wherein R, $R_0$, and $R_3$ are hydrogen or alkyl of 1 to 3 carbon atoms, inclusive; wherein $R_1$ and $R_2$ are alkyl of 1 to 3 carbon atoms or the group

together is pyrrolidino, piperidino, morpholino and N-methylpiperazerino; $R_7$ is 2-pyridyl or a phenyl radical of the formula

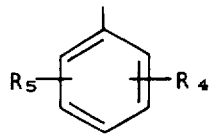

wherein $R_4$ is hydrogen, fluoro, or chloro; wherein $R_5$ is hydrogen or fluoro, with the proviso that $R_5$ is not fluoro, when $R_4$ is chloro; wherein $R_6$ is hydrogen, chloro, fluoro, bromo, trifluoromethyl, or nitro, which comprises: heating between 75°–120°C. a compound of formula I

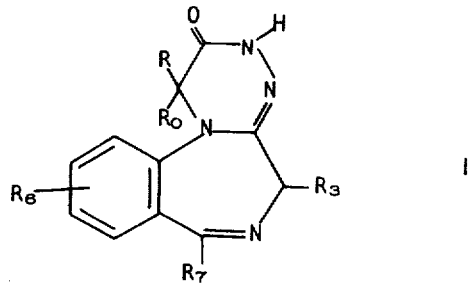

wherein R, $R_0$, $R_3$, $R_6$, and $R_7$ are defined as above with a strong base in an inert organic solvent, and then with a compound of the formula III

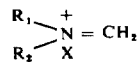

wherein $R_1$ and $R_2$ are defined as above and X is a chlorine or bromine ion, to obtain the compound of formula II above.

13. The process of claim 12, wherein the strong base is sodium hydride.

14. The process of claim 12, wherein the compound III is dimethylmethyleneammonium chloride.

15. The process of claim 12, wherein starting compound I is 9-chloro-7-(o-chlorophenyl)-3,5-dihydro-as-triazino-[4,3-a][1,4]benzodiazepin-2(1H)-one.

* * * * *

UNITED STATES PATENT AND TRADEMARK OFFICE
CERTIFICATE OF CORRECTION

PATENT NO. : 3,933,816  
DATED : Jan. 20, 1976  
INVENTOR(S) : Jacob Szmuszkovicz Page 1 of 3

It is certified that error appears in the above–identified patent and that said Letters Patent are hereby corrected as shown below:

Face page, title, "[4,3-A][1,5]" should read -- [4,3-a][1,5] --.
Column 1, line 3, title, "TRIAZINO[4,3-A]" should read
    -- TRIAZOLO[4,3-a] --.
Column 2, line 34, "$R_5$ is not fluoro, when $R_4$" should read
    -- $R_5$ is hydrogen or fluoro, with the proviso that $R_5$
    is not fluoro, when $R_4$ --.
Column 6, line 35, "an addiitional" should read -- an
    additional --.
Column 7, line 21, "methyl)-b 2,3-" should read
    -- methyl)-2,3- --.
Column 8, line 12, "2-bormopropionate" should read
    -- 2-bromopropionate --.
Column 8, lines 30-31, "5-o-chlorophenyl)-127    3-ethyl-2H"
    should read -- 5-(o-chlorophenyl)-3-ethyl --.
Column 9, line 42, "2oxo-" should read -- 2-oxo- --.
Column 9, line 48, "3ethyl-2,3" should read -- 3-ethyl-2,3 --.
Column 13, line 44, "azepin-lacetic acid" should read
    -- azepin-1-acetic acid --.
Column 14, line 5, "-2thioxo-7" should read -- -2-thioxo-7 --.
Column 14, line 31, "dihydroas-" should read -- dihydro-as- --.
Column 14, line 50, "dihydroas-" should read -- dihydro-as- --.
Column 15, line 51, "benzo-diazepin" should read
    -- benzodiazepin --.
Column 15, line 57, "dihydroas-" should read -- dihydro-as- --.
Column 17, line 53, "[4,3-a]-[1,4]" should read -[4,3-a][1,4]-.
Column 17, line 58, "[4,3-a]-[1,4]" should read -- [4,3-a][1,4]--.
Column 17, line 64, "[4,3-a]-[1,4]" should read -- [4,3-a][1,4]--.
Column 17, line 66, "[4,3-a]-[1,4]" should read -- [4,3-a][1,4]--.
Column 17, line 68, "[4,3-a]-[1,4]" should read -- [4,3-a][1,4]--.
Column 18, line 10, "[4,3-a]-[1,4]" should read -- [4,3-a][1,4]--.

UNITED STATES PATENT AND TRADEMARK OFFICE
CERTIFICATE OF CORRECTION

PATENT NO. : 3,933,816
DATED : Jan. 20, 1976
INVENTOR(S) : Jacob Szmuszkovicz

It is certified that error appears in the above—identified patent and that said Letters Patent are hereby corrected as shown below:

Column 18, line 40, "chloride (freshy" should read
-- chloride (freshly --.
Column 18, line 42, "steambath or 20 hours" should read
-- steambath for 20 hours --.
Column 18, line 68, "point. ether cloudiness" should read
-- point. --.
Column 19, line 1, "The ther filtrate" should read
-- The ether filtrate --.
Column 19, line 4, "to cludiness" should read -- to cloudiness--.
Column 19, line 19, "dimethyl-amino" should read
-- dimethylamino --.
Column 19, line 24, "dimethyl-amino" should read
-- dimethylamino --.
Column 20, line 1, "[4,3-a]-[1,4]" should read --
-- [4,3-a][1,4] --.
Column 20, line 18, "7-(2pyridyl" should read -- 7-(2-pyridyl --
Column 20, line 25, "pyridyl)13-" should read -- pyridyl)-3- --.
Column 20, line 60, "(O-chloro" should read -- (o-chloro --.
Column 20, line 65, "[1,4]benz9diazepin-" should read
-- [1,4]benzodiazepin- --.
Column 21, line 55, "methyl)13,5-" should read -- methyl)-3,5- --
Column 21, line 63, "Examaple" should read -- Example --.
Column 22, line 16, "acetly chloride" should read
-- acetyl chloride --.
Column 22, line 56, "to bis(4-" should read -- To bis(4- --.
Column 23, line 24, "A][1,4]" should read -- a][1,4] --.
Column 23, line 53, "amino)-methyl" should read
-- amino)methyl --.

UNITED STATES PATENT AND TRADEMARK OFFICE
CERTIFICATE OF CORRECTION

PATENT NO. : 3,933,816
DATED : Jan. 20, 1976
INVENTOR(S) : Jacob Szmuszkovicz

It is certified that error appears in the above-identified patent and that said Letters Patent are hereby corrected as shown below:

Column 25, line 3, "wheein $R(_6$" should read -- wherein $R'_6$ --.
Column 25, line 41, "[1,49" should read -- [1,4] --.
Column 26, line 1, "$B_6$ is 9-" should read -- $R_6$ is 9- --.
Column 26, lines 25-28, "$N\genfrac{}{}{0pt}{}{\phantom{R_1}}{R_2}R_1$" should read -- $N\genfrac{}{}{0pt}{}{R_1}{R_2}$ --.

Signed and Sealed this

*Twenty-fifth* Day of *September 1979*

[SEAL]

*Attest:*

*Attesting Officer*

LUTRELLE F. PARKER
*Acting Commissioner of Patents and Trademarks*